(12) United States Patent
Aase et al.

(10) Patent No.: US 11,896,436 B2
(45) Date of Patent: *Feb. 13, 2024

(54) METHOD AND SYSTEM FOR PROVIDING STANDARD ULTRASOUND SCAN PLANE VIEWS USING AUTOMATIC SCAN ACQUISITION ROTATION AND VIEW DETECTION

(71) Applicant: GE Precision Healthcare LLC, Wauwatosa, WI (US)

(72) Inventors: Svein Arne Aase, Trondheim (NO); Kristin McLeod, Oslo (NO); Anders Sornes, Oslo (NO)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/972,311

(22) Filed: Oct. 24, 2022

(65) Prior Publication Data
US 2023/0043109 A1 Feb. 9, 2023

Related U.S. Application Data

(63) Continuation of application No. 16/351,792, filed on Mar. 13, 2019, now Pat. No. 11,517,290.

(51) Int. Cl.
*A61B 8/00* (2006.01)
*A61B 8/08* (2006.01)

(52) U.S. Cl.
CPC ............. *A61B 8/54* (2013.01); *A61B 8/4461* (2013.01); *A61B 8/4488* (2013.01); *A61B 8/461* (2013.01); *A61B 8/469* (2013.01); *A61B 8/523* (2013.01)

(58) Field of Classification Search
None
See application file for complete search history.

(56) References Cited

U.S. PATENT DOCUMENTS

| 7,648,460 B2 | 1/2010 | Simopoulos et al. |
| 2012/0065510 A1 | 3/2012 | Snare et al. |

(Continued)

FOREIGN PATENT DOCUMENTS

| EP | 2982306 | 10/2017 |

OTHER PUBLICATIONS

Ostvik, Andreas et al., "Real-time Standard View Classification in Transthoracic Echocardiography Using Convolutional Neural Networks," Norwegian University of Science and Technology, Aug. 14, 2018, pp. 1-15, Norway.

(Continued)

*Primary Examiner* — Yi-Shan Yang
*Assistant Examiner* — Marjan Saboktakin
(74) *Attorney, Agent, or Firm* — McAndrews, Held & Malloy, Ltd.; Daniel Bissing; David Bates (57) ABSTRACT

A system and method for acquiring standard ultrasound scan plane views is provided. The method includes acquiring a scan plane by an ultrasound probe positioned at a scan position over a region of interest. The method includes identifying the scan plane as a first standard view. The method includes automatically adjusting a scan acquisition angle until a second standard view is determined. The adjusting the scan acquisition angle includes rotating and/or tilting the scan acquisition angle. The method includes acquiring, by the ultrasound probe positioned at the scan position, an additional scan plane at the adjusted scan acquisition angle until the second standard view is determined. The method includes automatically determining whether the additional scan plane is the second standard (Continued)

view. The method includes presenting the additional scan plane having the second standard view at a display system.

23 Claims, 4 Drawing Sheets

(56) References Cited

U.S. PATENT DOCUMENTS

2015/0302638 A1 10/2015 Jago et al.
2016/0206281 A1 7/2016 Zou et al.

OTHER PUBLICATIONS

Voluson Expert Series, "Voluson™ E6, Voluson™ E8, Voluson™ E10, Instructions for Use H48711BH Revision 4," 2018 General Electric, 7 pages.

METHOD AND SYSTEM FOR PROVIDING STANDARD ULTRASOUND SCAN PLANE VIEWS USING AUTOMATIC SCAN ACQUISITION ROTATION AND VIEW DETECTION

CROSS-REFERENCE TO RELATED APPLICATIONS/INCORPORATION BY REFERENCE

This application is a continuation of U.S. patent application Ser. No. 16/351,792, filed Mar. 13, 2019, the contents of which are hereby incorporated herein by reference in its entirety.

FIELD

Certain embodiments relate to ultrasound imaging. More specifically, certain embodiments relate to a method and system for providing standard ultrasound scan plane views. In various embodiments, an acquisition scan plane is automatically rotated without rotation of the ultrasound probe until an acceptable, desired standard scan plane is detected for presentation at a display system.

BACKGROUND

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images.

In various applications, the acquisition of one or more standard scan planes may be performed to provide a medical diagnosis. For example, a transthoracic echocardiogram may involve acquiring ultrasound images that include a number of standard views, such as a four chamber (4CH) view, a two chamber (2CH) view, an apical long axis (APLAX) view, and the like. To acquire the desired standard views, an ultrasound operator may manipulate the probe to an image acquisition position, such as an apical window over the apex of a heart. The ultrasound operator may manually rotate the probe to different rotational positions to acquire the different standard views. However, the manual rotation of the ultrasound probe may cause the probe to glide away from the apical window. Additionally, the manual rotation of the probe on ribs of a patient may cause discomfort to the patient. The ultrasound operator may also have difficulty locating certain standard views, such as the 2CH view, because the probe is rotated to a position partly covering ribs of the patient. The rotation of the probe to the position partly covering the ribs may also degrade image quality. For example, the ribs of the patient may reduce the effective aperture of the probe and possibly contribute to reflection artifacts.

Instead of manually rotating an ultrasound probe to individually acquire the ultrasound scan planes of the desired standard views, an ultrasound operator may acquire one or more full 3D ultrasound volumes of a region of interest, such as the heart. The standard viewing planes may subsequently be detected in the 3D volume and presented at a display system for analysis. However, 3D ultrasound is more complicated and time-consuming to set-up. Moreover, the frame rate is usually much lower than in 2D or thin slab ultrasound, resulting in the physical resolution of an image plane being much lower. 3D ultrasound also records substantially more ultrasound data and much of this data is unused to perform the needed analysis.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for acquiring standard ultrasound scan plane views, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Certain embodiments may be found in a method and system for acquiring standard ultrasound scan plane views. Various embodiments have the technical effect of acquiring standard ultrasound scan plane views by automatically rotating an acquisition scan plane without rotation of the ultrasound probe until an acceptable, desired standard scan plane is detected for presentation at a display system.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

Figure 1:
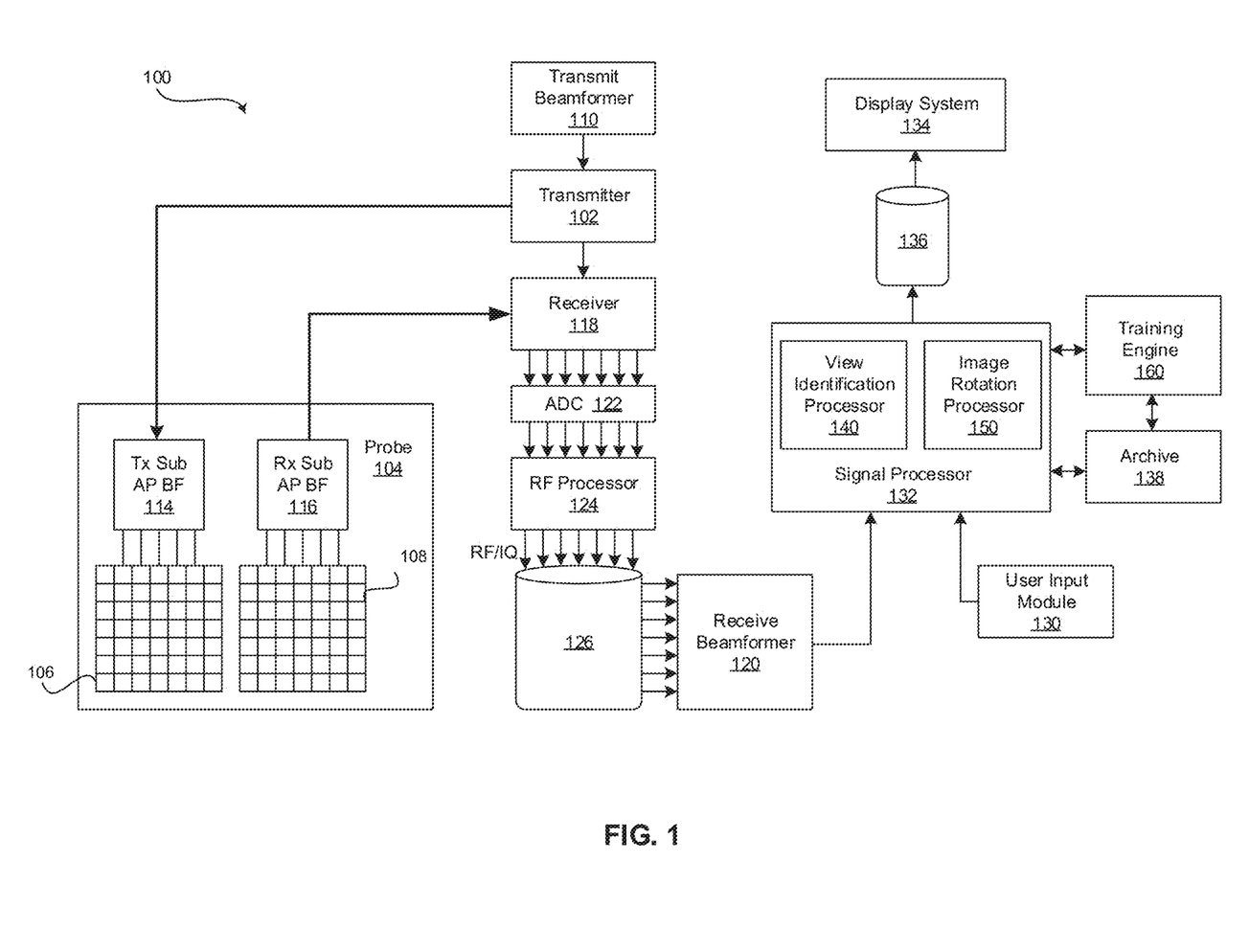
FIG. 1 is a block diagram of an exemplary ultrasound system that is operable to acquire standard ultrasound scan plane views, in accordance with various embodiments.

FIG. 1 is a block diagram of an exemplary ultrasound system that is operable to acquire standard ultrasound scan plane views, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input module 130, a signal processor 132, an image buffer 136, a display system 134, an archive 138, and a training engine 160.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as the heart, a blood vessel, or any suitable anatomical structure. The ultrasound probe 104 can be any suitable ultrasound probe operable to acquire ultrasound scan planes at different rotational and/or tilt angles without physically moving the ultrasound probe. In an exemplary embodiment, the ultrasound probe 104 may include a one dimensional transducer array that can be mechanically oriented in a plurality of orientations by a motor in response to instructions from the signal processor 132. In a preferred embodiment, the probe 104 includes a 2D array of ultrasound elements operable to electronically transmit ultrasonic signals and acquire ultrasound data in any orientation in three dimensional space, called a four dimensional (e4D) matrix probe. For example, the e4D ultrasound probe 104 may be the GE 4Vc-D four dimensional (4D) matrix cardiac probe. The processing of the acquired images in any steered direction can be performed partially or completely by probe-internal sub-aperture processing, by system side software beamforming, or by beamforming in hardware. In an exemplary embodiment, the acquired scan planes are either 2D images and/or thin slab images. For example, thin slab images may be acquired using multi-line acquisition (MLA) where a plurality of transmit beams are arranged spatially along a plane and multiple receive beams for each transmit beam are received orthogonal to a plane width of the transmit beams. In various embodiments, a thickness of the thin slab images may be 7 millimeters or less.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input module 130 may be utilized to input patient data, scan parameters, settings, select protocols and/or templates, select one or more desired standard views, provide a command for storing a displayed scan plane, and the like. In an exemplary embodiment, the user input module 130 may be operable to configure, manage and/or control operation of one or more components and/or modules in the ultrasound system 100. In this regard, the user input module 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input module 130, the signal processor 132, the image buffer 136, the display system 134, and/or the archive 138. The user input module 130 may include button(s), rotary encoder(s), a touchscreen, motion tracking, voice recognition, a mousing device, keyboard, camera and/or any other device capable of receiving a user directive. In certain embodiments, one or more of the user input modules 130 may be integrated into other components, such as the display system 134, for example. As an example, user input module 130 may include a touchscreen display.

In various embodiments, a protocol and/or one or more desired standard views may be selected during or at the onset of an imaging procedure in response to a directive received via the user input module 130. For example, an ultrasound operator may identify a transthoracic echocardiogram acquired at an apical window protocol at an onset of an imaging procedure via the user input module 130. The protocol may include a number of pre-defined standard views, such as a four chamber (4CH) view, a two chamber (2CH) view, an apical long axis (APLAX) view, and the like. The selected protocol may be provided via the user input module 130 to the signal processor 132 so that the signal processor 132 may apply view detection processing and acquisition rotation and/or tilt parameters. The view detection processing applied by the signal processor 132 may automatically detect each of the standard views. The acquisition rotation and/or tilt parameters may be applied by the signal processor 132 to automatically rotate and/or tilt scan plane acquisition to acquire each of the standard views once the ultrasound probe 104 is properly positioned at the apical window. As another example, an ultrasound operator may select automatic identification of a particular standard view, such as a 2CH view or any suitable view, during an imaging procedure so that the signal processor 132 may automatically rotate and/or tilt the scan plane acquisition from a current standard view, such as a 4CH view, until an acceptable scan plane of the desired 2CH view is acquired by the probe 104.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise a view identification processor 140 and an image rotation processor 150 and may be capable of receiving input information from a user input module 130 and/or archive 138, generating an output displayable by a display system 134, and manipulating the output in response to input information from a user input module 130, among other things. The signal processor 132, view identification processor 140, and image rotation processor 150 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a view identification processor 140 that comprises suitable logic, circuitry, interfaces and/or code that may be operable to analyze an acquired ultrasound scan plane to determine whether a standard view is provided and if so, identify the particular standard view. The view identification processor 140 may include image detection algorithms, one or more deep neural networks (e.g., a convolutional neural network) and/or may utilize any suitable form of image detection techniques or machine learning processing functionality configured to automatically identify standard views of an anatomical structure provided in the ultrasound image data. For example, the view identification processor 140 may be made up of an input layer, an output layer, and one or more hidden layers in between the input and output layers. Each of the layers may be made up of a plurality of processing nodes that may be referred to as neurons. For example, the input layer may have a neuron for each pixel or a group of pixels from a scan plane of an anatomical structure. The output layer may have a neuron corresponding to each pre-defined standard view. As an example, if imaging a heart, the output layer may include neurons for a 4CH view, a 2CH view, an APLAX view, a parasternal long axis (PLAX) view, a short axis apical level (SAX-AP) view, a short axis papillary muscle level (SAX-PM) view, a short axis mitral valve level (SAX-MV) view, an unknown view, an other view, and/or any suitable view. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the view identification processor 140 deep neural network (e.g., convolutional neural network) may identify standard views of an anatomical structure in ultrasound image data with a high degree of probability.

The view identification processor 140 may be configured to provide information regarding the view type and/or view quality of the currently acquired scan plane to an image rotation processor 150 of the signal processor 132. In various embodiments, the view identification processor 140 may be configured to automatically store an acceptable or best standard view once detected. The acceptable or best detected standard view may be stored at archive 138 or any suitable data storage medium. Additionally and/or alternatively, the view identification processor 140 may be configured to store an acquired scan plane of a desired standard view in response to a user input via the user input module 130 and/or in response to a user or default setting, such as an elapsed viewing time of a standard view at the display system 134.

The signal processor 132 may include an image rotation processor 150 that comprises suitable logic, circuitry, interfaces and/or code that may be operable to automatically rotate and/or tilt the acquisition of the scan plane to obtain a desired and acceptable or best standard view. The image rotation processor 150 may be configured to provide a rotation and/or tilt of a pre-defined angle or range of angles corresponding with a selected standard view. For example, in response to an instruction to acquire a 2CH view of a heart after an ultrasound probe 104 is manually positioned at the apical window of a patient and a 4CH view is acquired as identified by the view identification processor 140, the image rotation processor 150 may automatically rotate the scan plane acquisition angle a pre-defined amount, such as −60 degrees (i.e., 60 degrees rotation in a counter-clockwise direction) from the 4CH view, to acquire a scan plane. In various embodiments, the view identification processor 140 may be configured to analyze the acquired scan plane to determine whether an acceptable 2CH view was acquired. The view identification processor 140 may be configured to provide information regarding the view type and/or view quality of the currently acquired scan plane to the image rotation processor 150. If a scan plane having an acceptable 2CH view has been acquired, the scan play may be presented at the display system 134. If the acquired scan plane does not provide an acceptable 2CH view, the image rotation processor 150 may iteratively acquire additional scan planes that are analyzed by the view identification processor 140 until an acceptable 2CH view is identified.

In various embodiment, an acceptable standard view provided by a scan plane may be defined by one of a plurality of modes. For example, an acceptable standard view may be a first standard view, an estimated best standard view, or a best standard view, among other things. The first standard view mode involves presenting the first selected standard view provided in a scan plane as identified by view identification processor 140. As an example, if the image rotation processor 150 rotates the acquisition scan plane −60 degrees from the 4CH view and the corresponding acquired scan plane provides a 2CH as identified by the view identification processor 140, the scan plane is presented at the display system 134. If the scan plane does not provide a 2CH view, the image rotation processor 150 acquires additional scan planes at different rotational angles until a 2CH view is identified by the view identification processor 140. For example, if a 2CH view is provided at a particular patient from −44 to −58 degrees of rotation from the 4CH view, the image rotation processor may acquire scan planes at −60 degrees, −40 degrees, −80 degrees, and −50 degrees. The view identification processor 140 would identify the scan plane acquired at the −50 degrees of rotation as having a 2CH view and that scan plane is presented at the display system 134. In other words, the image rotation processor 150 may stop acquiring scan planes at different angles of rotation from the 4CH view once a first scan plane having a 2CH view is acquired as identified by the view identification processor 140. In various embodiments, the first standard view mode may be the most efficient manner of obtaining the desired standard view but may not provide a best scan plane. For example, if a 2CH view is provided at a particular patient from −44 to −58 degrees of rotation from the 4CH view and the best 2CH view is provided at −52 degrees, the first acquired scan plane having the 2CH view at −50 degrees in the above example may not be the most desirable view.

The estimated best standard view mode involves identifying the outer edges in a range of angles for a particular standard view of a particular patient and selecting the scan plane at the angle in the middle of the identified range. For example, if a 2CH view is provided at a particular patient from −44 to −58 degrees of rotation from the 4CH view, the image rotation processor may acquire scan planes at −60 degrees, −40 degrees, −80 degrees, −50 degrees, −55 degrees, −58 degrees, −59 degrees, −45 degrees, −43, degrees, and −44 degrees. The view identification processor 140 would identify the scan planes acquired at the −44 and −58 degrees of rotation as having the outer edges of 2CH views and would select the scan plane in the middle of that range (i.e., the scan plane at −51 degrees) for presentation at the display system 134. In other words, the image rotation processor 150 may stop acquiring scan planes at different angles of rotation from the 4CH view once the outer edges of a range of angles for a particular standard view plane of a particular patient are identified by the view identification processor 140. In various embodiments, the estimated best standard view mode may be less efficient than the first standard view mode for obtaining the desired standard view but may provide a scan plane having a better view quality. For example, if the best 2CH view is provided at −52 degrees, the scan plane provided at −51 degrees by the estimated best standard view mode may be a higher quality view than the scan plane acquired at −50 degrees using the first standard view mode in the above examples.

The best standard view mode involves identifying all angles for a particular standard view of a particular patient and selecting the scan plane identified as having the highest quality by the view identification processor 140. For example, if a 2CH view is provided at a particular patient from −44 to −58 degrees of rotation from the 4CH view with the scan plane at 52 degrees having the highest quality, the image rotation processor 150 may acquire scan planes at −60 degrees, −40 degrees, −80 degrees, −50 degrees, −51 degrees, −52 degrees, −53 degrees, −54 degrees, −55 degrees, −56 degrees, −57 degrees, −58 degrees, −59 degrees, −49 degrees, −48 degrees, −47 degrees, −46 degrees, −45 degrees, −44 degrees, and −43 degrees. The view identification processor 140 would identify the scan planes acquired at the −44 through −58 degrees of rotation as providing 2CH views and would select the scan plane having the highest quality (i.e., the scan plane at −52 degrees) for presentation at the display system 134. In other words, the image rotation processor 150 may stop acquiring scan planes at different angles of rotation from the 4CH view once all of the scan planes providing a particular standard view plane of a particular patient are identified by the view identification processor 140. In various embodiments, the best standard view mode may be less efficient than both of the first standard view mode and the estimated best standard view mode for obtaining the desired standard view but may provide a scan plane having a highest view quality.

Figure 2:
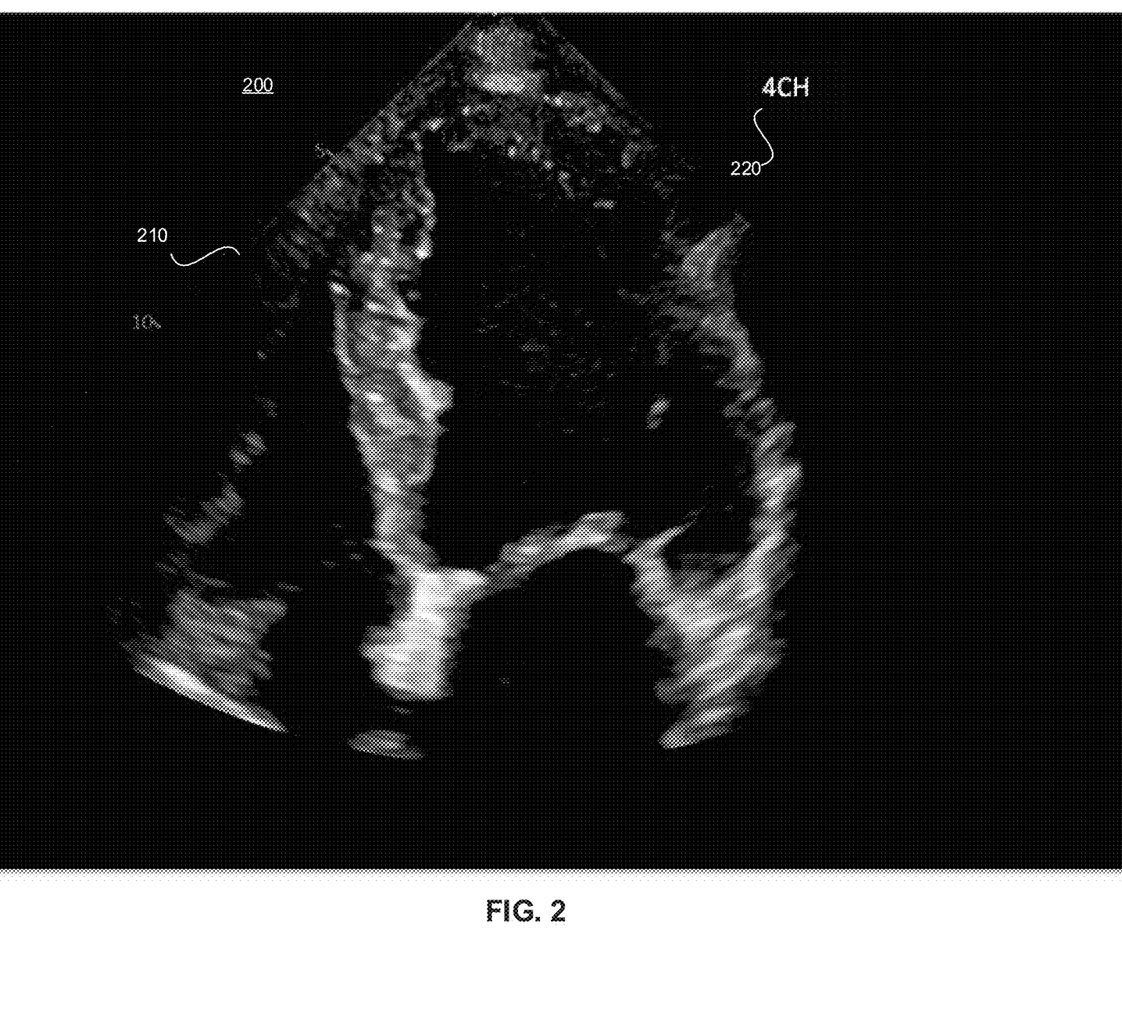
FIG. 2 is a display of an exemplary standard ultrasound scan plane, in accordance with various embodiments.
Figure 3:
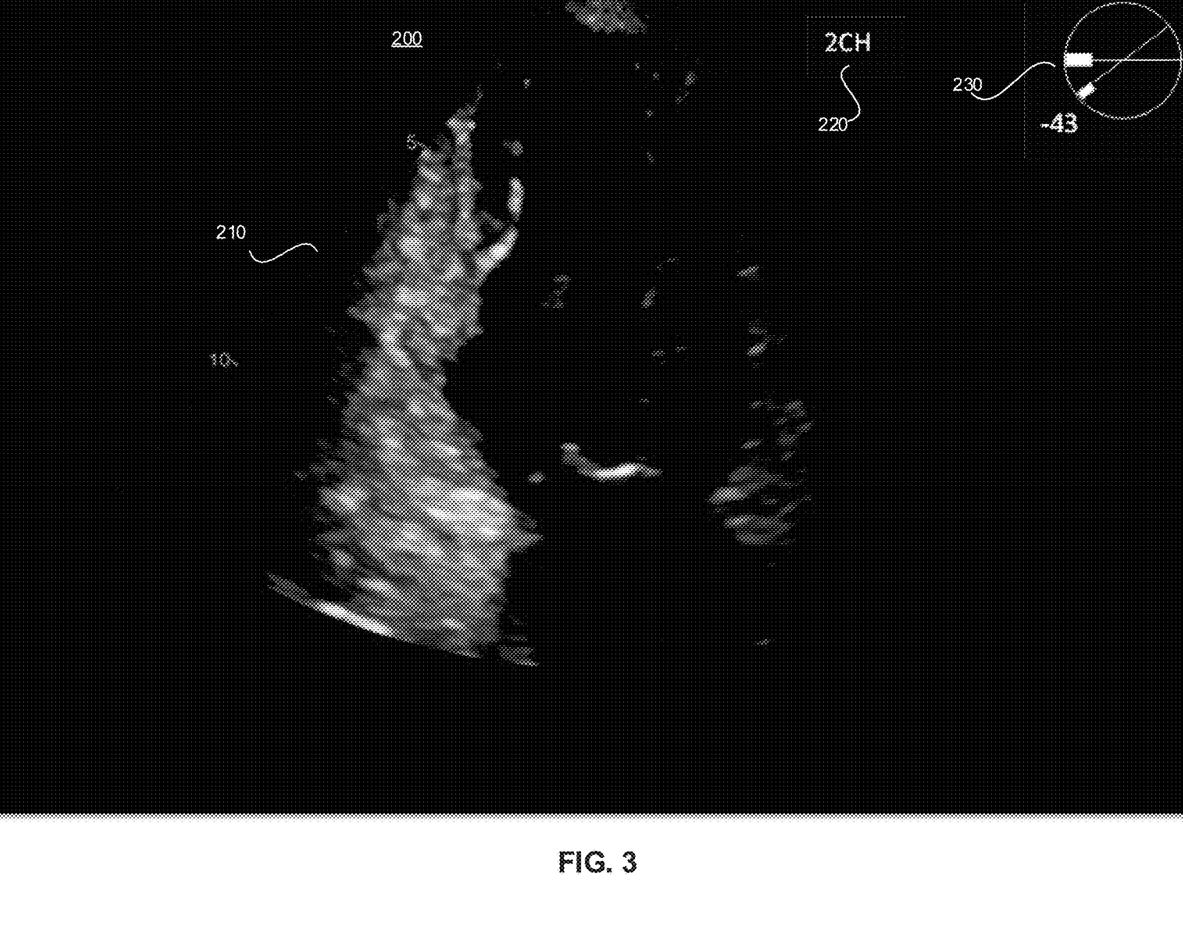
FIG. 3 is a display of an exemplary standard ultrasound scan plane, in accordance with various embodiments.

FIGS. 2 and 3 are displays 200 of exemplary standard ultrasound scan planes 210, in accordance with various embodiments. Referring to FIGS. 2 and 3, each display 200 includes a scan plane 210 corresponding to a standard view, a view identifier 220, and an angle of rotation 230 from a previous or primary standard view (if applicable). Referring to FIG. 2, an ultrasound operator may manually move an ultrasound probe 104 to acquire a scan plane of a standard view. For example, the ultrasound operator may manually move the probe 104 to the apical window over the apex of a heart of the patient. The probe 104 acquires scan planes that are processed by the signal processor 132 and presented at the display system 134. The signal processor 132 may present the standard view 210 at the display 200 of the display system 134 once the probe 104 is appropriately positioned. The signal processor 132 may update the display 200 to provide a view identifier 220 corresponding to the standard view detected by the signal processor 132. As an example, the scan plane 210 of a 4CH standard view is presented at the display 200 along with the view identifier 220 specifying the 4CH standard view in FIG. 2.

After a first standard view is acquired and presented at display 200 as shown in FIG. 2, an additional standard view, different from the first standard view, may be automatically acquired and presented at the display 200 in response to, for example, a view selection provided via the user input module 130, a selected protocol, or the like. Referring to FIG. 3, the signal processor 132 may automatically rotate the scan plane acquisition a pre-defined amount from the 4CH view, such as −60 degrees (i.e., 60 degrees rotation in a counter-clockwise direction), to acquire the additional scan plane. The signal processor 132 applies image detection techniques to determine whether an acceptable 2CH standard view is present in the acquired scan plane. The signal processor 132 presents the scan plane at the display 200 of the display system 132 if an acceptable 2CH standard view is identified. If an acceptable 2CH standard view is not present in the acquired scan plane, the signal processor 132 iteratively rotates the scan plane acquisition until an acceptable 2CH standard view is identified. For example, the signal processor 132 may control the ultrasound system 100 to acquire scan planes at −60 degrees, −40 degrees, −80 degrees, −50 degrees, −45 degrees, and −43 degrees. The signal processor 132 may identify the scan plane acquired at −43 degrees rotation from the 4CH standard view is an acceptable 2CH standard view. The scan plane 210 corresponding with the acceptable 2CH standard view is presented at the display 200 of the display system 132. The signal processor 132 may update the display 200 to provide a view identifier 220 corresponding to the standard view detected by the signal processor 132. As an example, the scan plane 210 of a 2CH standard view is presented at the display 200 along with the view identifier 220 specifying the 2CH standard view in FIG. 3. In various embodiments, the angle of rotation 230 from the previous or primary standard view may be presented at the display 200 of the display system 134. According to the above example, the scan plane 210 of the 2CH standard view is presented at the display 200 with a view identifier 220 specifying the 2CH standard view and the −43 degree angle of rotation 230 as shown in FIG. 3.

Referring again to FIG. 1, the display system 134 may be any device capable of communicating visual information to a user. For example, a display system 134 may include a liquid crystal display, a light emitting diode display, and/or any suitable display or displays. The display system 134 can be operable to present a display 200 of information from the signal processor 132 and/or archive 138, such as ultrasound scan planes 210, view identifiers 220, an angle of rotation 230 (if applicable), and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores medical image data, image detection instructions, and acquisition rotation and tilt instructions, for example.

Still referring to FIG. 1, the training engine 160 may comprise suitable logic, circuitry, interfaces and/or code that may be operable to train the neurons of the deep neural network(s) of the view identification processor 140 to automatically identify standards view of an anatomical structure provided in an ultrasound scan plane. For example, the training engine 160 may train the deep neural networks of the view identification processor 140 using databases(s) of classified scan planes. As an example, a view identification processor 140 deep neural network may be trained by the training engine 160 with scan planes of particular standard view of a particular anatomical structure to train the view identification processor 140 with respect to the characteristics of the particular standard view of the anatomical structure, such as the appearance of structure edges, the appearance of structure shapes based on the edges, the positions of the shapes relative to landmarks in the ultrasound image data, and the like. In certain embodiments, the anatomical structure may be a heart and the standard views may include, among other things, a 4CH view, a 2CH view, an APLAX view, a PLAX view, a SAX-AP view, a SAX-PM view, a SAX-MV view, and/or any suitable standard view of the heart. The structural information may include information regarding the edges, shapes, and positions of ventricles, atria, papillary muscles, inferior wall, mitral valve, apex, septum, and/or the like. In various embodiments, the databases of training scan planes may be stored in the archive 138 or any suitable data storage medium. In certain embodiments, the training engine 160 and/or training image databases may be external system(s) communicatively coupled via a wired or wireless connection to the ultrasound system 100.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input module 130 may be integrated as a touchscreen display.

Figure 4:
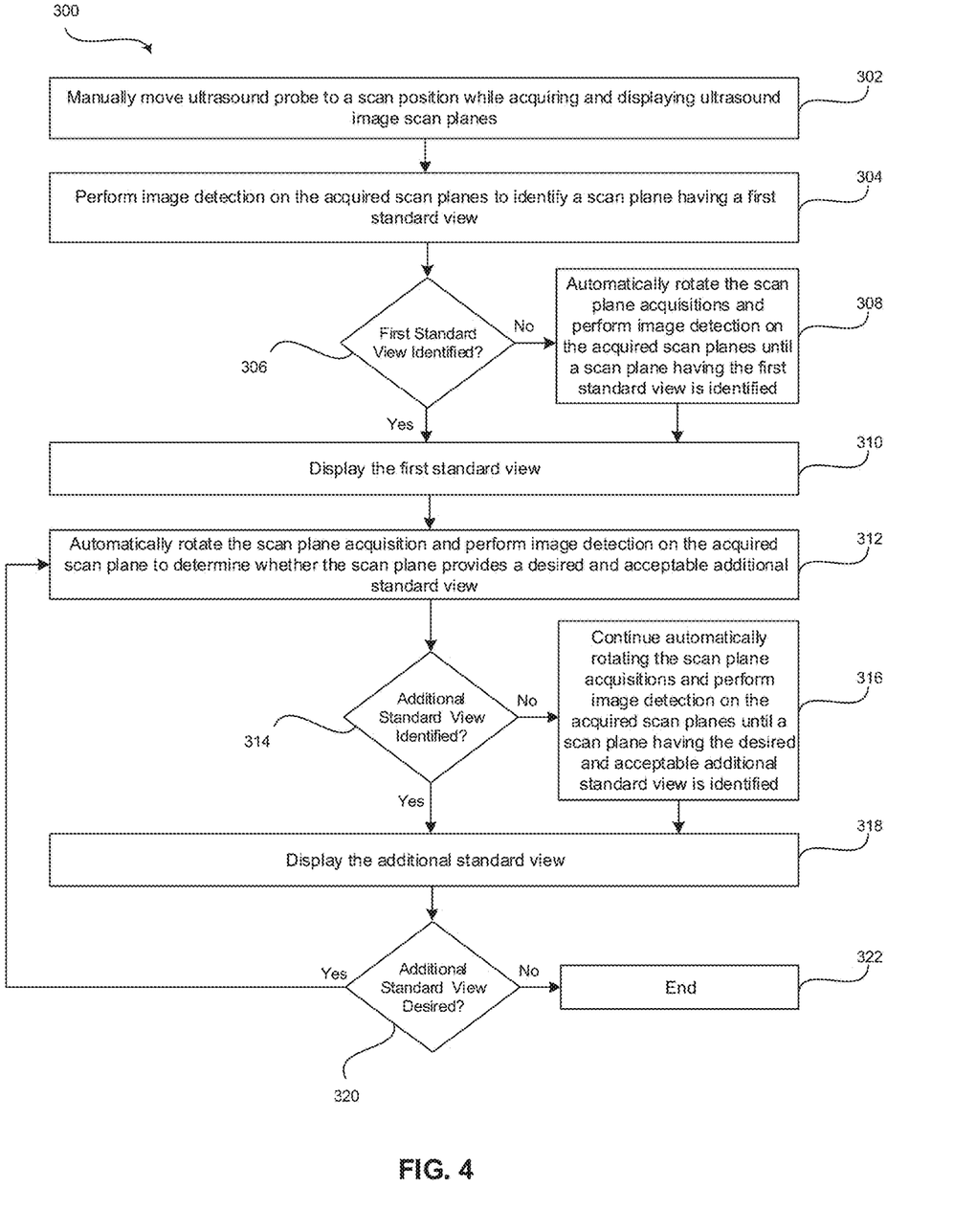
FIG. 4 is a flow chart illustrating exemplary steps that may be utilized for acquiring standard ultrasound scan plane views, in accordance with various embodiments.

FIG. 4 is a flow chart 300 illustrating exemplary steps 302-322 that may be utilized for acquiring standard ultrasound scan plane views 210, in accordance with various embodiments. Referring to FIG. 4, there is shown a flow chart 300 comprising exemplary steps 302 through 322. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 302, a probe 104 of an ultrasound system 100 may be manually moved to a scan position while acquiring and displaying ultrasound image scan planes 210. For example, the ultrasound system 100 may acquire scan planes with an ultrasound probe 104 positioned at a scan position over region of interest, such as an apical window or a parasternal window over a heart.

At step 304, the signal processor 132 of the ultrasound system 100 may process the acquired scan planes to detect whether the acquired scan planes include a first standard view. For example, a view identification processor 140 of the signal processor 132 may receive the scan planes acquired by probe 104 at step 302. The view identification processor 140 may perform image detection on the acquired scan planes 210 to identify a scan plane 210 having a first standard view. The view identification processor 140 may apply image detection algorithms, one or more deep neural networks (e.g., a convolutional neural network) and/or may utilize any suitable form of image detection techniques or machine learning processing functionality configured to automatically identify standard views of an anatomical structure provided in the acquired scan planes. The standard view may correspond with an ultrasound probe position and/or an anatomical structure being scanned. As an example, the anatomical structure may include a heart, fetus, or any suitable anatomical structure. The scan position if imaging a heart may include a parasternal window, an apical window, or any suitable scan position. The standard views when acquiring scan planes of the heart from a parasternal window may include, for example, a PLAX view, a SAX-AP view, a SAX-PM view, a SAX-MV view, and/or the like. The standard views when acquiring scan planes of the heart from an apical window may include, for example, a 4CH view, a 2CH view, an APLAX view, and/or the like.

At step 306, the signal processor 132 of the ultrasound system 100 may determine whether a first standard view has been identified. For example, the view identification processor 140 of the signal processor 132 performs image detection on the acquired scan planes as described in step 304. The process proceeds to step 310 once the view identification processor 140 identifies an acceptable standard view 210. In various embodiments, an option may be selected by an ultrasound operator and/or automatically selected after a predetermined elapsed time for system assisted standard view location. For example, an ultrasound operator may provide a system assistance instruction via a user input module 130, an option could be presented for selecting system assistance after a predetermined period of time, and/or system assistance may be automatically selected after an elapsed time of an ultrasound operator manually searching for a standard view, among other things. The process may proceed to step 308 if a first standard view is not identified by the view identification processor 140 and a system assistance option is manually or automatically selected. Additionally and/or alternatively, steps 302 through 306 may be repeated until the ultrasound operator manually positions the probe 104 at a position to acquire a scan plane 210 having a first standard view as identified by the view identification processor 140.

At step 308, the signal processor 132 of the ultrasound system 100 may automatically rotate the scan plane acquisitions and perform image detection on the acquired scan planes until a scan plane 210 having the first standard view is identified. For example, an image rotation processor 150 of the signal processor 132 may iteratively rotate the scan plane acquisition angle such that scan planes at different acquisition angles may be acquired by an ultrasound probe 104 held in a fixed position. The view identification processor 140 performs image detection on the scan planes acquired at the different acquisition angles until the first standard view is identified. In various embodiments, the image rotation processor 150 may additionally and/or alternatively tilt the scan plane acquisition angle in azimuth and/or elevation directions such that planes at different acquisition rotational and/or tilt angles may be acquired by an ultrasound probe 104 held in a fixed position. The view identification processor 140 performs image detection on the scan planes acquired at the different acquisition rotational and/or tilt angles until the first standard view is identified.

At step 310, the signal processor 132 of the ultrasound system 100 may display the first standard view acquired at step 304 or 308. For example, the signal processor 132 may present the scan plane 210 of the standard view on a display 200 of a display system 134. In various embodiments, the signal processor 132 may store the scan plane of the standard view at archive 138 or any suitable data storage medium. The scan plane of the standard view may be stored automatically when identified by the view identification processor 140, in response to an ultrasound operator selection via user input module 130, after a predetermined elapsed viewing time at the display system 134, or the like.

At step 312, the signal processor 132 of the ultrasound system 100 may automatically rotate the scan plane acquisition and perform image detection on the acquired scan plane to determine whether the scan plane provides a desired and acceptable additional standard view. For example, the signal processor 132 may be executing a protocol specifying a set of standard views to acquire, present, and store. After acquiring, identifying, presenting, and storing a scan plane 210 having the first standard view at steps 302 through 310, the signal processor may proceed to acquire and identify a next view according to the protocol. As another example, the signal processor 132 may receive an ultrasound operator instruction via user input module 130 for acquiring a selected standard view and may proceed to acquire and identify the selected view according to the selection. An image rotation processor 150 of the signal processor 132 may rotate the scan plane acquisition angle from the scan plane having the first standard view by a predetermined amount corresponding with an expected scan acquisition angle of the additional standard view. For example, if the first standard view is a 4CH view and the additional standard view is a 2CH view, the image rotation processor 150 may rotate the scan plane acquisition angle –60 degrees from the 4CH view. As another example, if the first standard view is a 4CH view and the additional standard view is an APLAX view, the image rotation processor 150 may rotate the scan plane acquisition angle –120 degrees from the 4CH view. The rotated scan planes are acquired by an ultrasound probe 104 held in a fixed position, as opposed to manually rotating a probe by an ultrasound operator. The view identification processor 140 performs image detection on the scan plane acquired at the predetermined acquisition angle.

At step 314, the signal processor 132 of the ultrasound system 100 determines whether a desired, acceptable, additional standard view has been identified. In various embodiments, the acceptability of the scan plane may be based on a selected or default acceptance mode of the system. For example, an acceptable standard view may be a first standard view, an estimated best standard view, or a best standard view, among other things. The first standard view mode involves presenting the first selected standard view provided in a scan plane as identified by view identification processor 140. As an example, if the scan plane acquisition at –60 degrees rotation is identified as providing the desired standard view by the view identification processor 140 at step 314, the process proceeds to step 318. If the scan plane acquisition at –60 degrees rotation does not provide the desired standard view as determined by the view identification processor 140 at step 314, the process 300 proceeds to step 316.

The estimated best standard view mode involves identifying the outer edges in a range of angles for a particular standard view of a particular patient and selecting the scan plane at the angle in the middle of the identified range. According to this mode, multiple scan plane acquisitions are performed to identify the scan plane acquisition angles corresponding with the outer edges having the desired standard view. The process 300 proceeds to step 316 to identify the desired, acceptable, additional standard view 210 if performing the estimated best standard view mode.

The best standard view mode involves identifying all angles for a particular standard view of a particular patient and selecting the scan plane identified as having the highest quality by the view identification processor 140. According to this mode, multiple scan plane acquisitions are performed to identify the highest quality scan plane acquisition angle corresponding with the desired standard view. The process 300 proceeds to step 316 to identify the desired, acceptable, additional standard view 210 if performing the best standard view mode.

At step 316, the signal processor 132 of the ultrasound system 100 may continue automatically rotating the scan plane acquisitions and perform image detection on the acquired scan planes until a scan plane having the desired and acceptable additional standard view is identified. For example, if the signal processor 132 is executing the first standard view acceptance mode and the scan plane acquired at step 312 did not provide the desired standard view as determined by the view identification processor 140, the image rotation processor 150 of the signal processor 132 may iteratively rotate the scan plane acquisition angle such that scan planes at different acquisition angles may be acquired. The view identification processor 140 performs image detection on the scan planes acquired at the different acquisition angles until the first standard view is identified. As another example, if the signal processor 132 is executing the estimated best standard view mode, the image rotation processor 150 may iteratively rotate the scan plane acquisition angle such that scan planes at different acquisition angles are acquired. The view identification processor 140 performs image detection on the scan planes acquired at the different acquisition angles until the outer edges and a scan plane in the middle of the outer edges is identified. As another example, if the signal processor 132 is executing the best standard view mode, the image rotation processor 150 may iteratively rotate the scan plane acquisition angle such that scan planes at different acquisition angles are acquired. The view identification processor 140 performs image detection on the scan planes acquired at the different acquisition angles until all scan planes having the desired standard view are identified. The view identification processor 140 applies image detection techniques to identify the desired standard view having the highest image quality. For example, the view identification processor 140 may select the scan plane having a closest match to a reference standard view and/or a least amount of image artifacts. The closest match to the reference standard view may be represented by a confidence level of a deep neural network (e.g., convolutional neural network) trained to recognize standard views.

In various embodiments, a tilt operation may be performed in addition to and/or as an alternative to the rotation operation. For example, if an ultrasound operator has positioned the ultrasound probe 104 at the parasternal window over a heart of a patient and acquired a scan plane providing a PLAX view as the first standard view at steps 302 through 310, the operator may desire to acquire one or more additional standard views, such as a SAX-AP view, a SAX-PM view, a SAX-MV view, and/or the like at steps 312 through 316. The image rotation processor 150 may rotate –90 degrees from the PLAX view to acquire a SAX view at step 312. If the pre-determined –90 degree scan plane acquisition does not provide an acceptable SAX view as identified by the view identification processor 140 at step 314, the image rotation processor 150 may iteratively rotate the scan plane acquisition until the view identification processor 140 identifies an acceptable scan plane of the SAX view at step 316. The rotation processor 150 may also iteratively perform a tilt operation from the SAX view in the azimuth and/or elevation directions until the view identification processor 140 identifies an acceptable scan plane of a SAX-MV view.

At step 318, the signal processor 132 of the ultrasound system 100 may display the additional standard view acquired at step 312 or 316. For example, the signal processor 132 may present the scan plane 210 of the standard view on a display 200 of a display system 134. In various embodiments, the signal processor 132 may store the scan plane of the standard view at archive 138 or any suitable data storage medium. The scan plane of the standard view may be stored automatically when identified by the view identification processor 140, in response to an ultrasound operator selection via user input module 130, after a predetermined elapsed viewing time at the display system 134, or the like.

At step 320, the signal processor 132 of the ultrasound system 100 determines whether an additional standard view is desired. For example, the signal processor 132 may be executing a protocol specifying a set of standard views to acquire, present, and store. After acquiring, identifying, presenting, and storing a scan plane 210 having the first standard view at steps 302 through 310 and an additional standard view at steps 312 through 318, the signal processor 132 may proceed to acquire and identify a next view according to the protocol by proceeding from step 320 to repeat steps 312 through 320. As another example, the signal processor 132 may receive an ultrasound operator instruction via user input module 130 for acquiring an additional selected standard view and may proceed to acquire and identify the selected view according to the selection by proceeding from steps 320 to repeat steps 312 through 320. The process 300 proceeds to step 322 if no additional standard views are desired. At step 322, the process 300 ends.

Aspects of the present disclosure provide a method 300 and system 100 for acquiring standard ultrasound scan plane views. In accordance with various embodiments, the method 300 may comprise acquiring 302, by an ultrasound probe 104 positioned at a scan position over a region of interest, a scan plane 210. The method 300 may comprise identifying 304, 306 the scan plane 210 as a first standard view. The method 300 may comprise automatically adjusting 312, 316, by at least one processor 132, 140, 150, a scan acquisition angle until a second standard view is determined 314, 316. The second standard view is different than the first standard view. The adjusting 312, 316 the scan acquisition angle may comprise at least one of rotating and tilting the scan acquisition angle. The method 300 may comprise acquiring 312, 316, by the ultrasound probe 104 positioned at the scan position, an additional scan plane 210 at the adjusted scan acquisition angle until the second standard view is determined. 314, 316. The method 300 may comprise automatically determining 312-316, by the at least one processor 132, 140, 150, whether the additional scan plane 210 is the second standard view. The method 300 may comprise presenting 318, at a display system 134, 200, the additional scan plane 210 having the second standard view.

In an exemplary embodiment, one or both of the scan plane 210 having the first standard view and the additional scan plane 210 having the second standard view is stored 310, 318 at a data storage medium 138. The storage 310, 318 at the data storage medium 138 may occur automatically, by the at least one processor 132, 140, in response to at least one of the scan plane 210 having the first standard view and the additional scan plane 210 having the second standard view being automatically identified. The storage 310, 318 at the data storage medium 138 may occur in response to an instruction received via a user input module 130. The storage 310, 318 at the data storage medium 138 may occur after at least one of the scan plane 210 having the first standard view and the additional scan plane 210 having the second standard view is presented at the display system 134, 200 for a predetermined amount of time. In certain embodiments, the automatically adjusting 132, 316 the scan acquisition angle and the acquiring 312, 316 the additional scan plane 210 is performed iteratively until the additional scan plane 210 having the second standard view is automatically determined 312-316 by the at least one processor 132, 140, 150.

In a representative embodiment, the identifying 304, 306 the scan plane 210 as the first standard view may be performed by the at least one processor 132, 140 applying machine learning algorithms to the scan plane 210. The automatically determining 312-316 whether the additional scan plane 210 is the second standard view is performed by the at least one processor 132, 140 applying the machine learning algorithms to the additional scan plane 210. In various embodiments, the additional scan plane 210 having the second standard view may be automatically determined 312-316 by the at least one processor 132, 140, 150 by selecting a first instance of the additional scan plane 210 having the second standard view. The additional scan plane 210 having the second standard view may be automatically determined 312-316 by the at least one processor 132, 140, 150 by identifying a range of scan acquisition angles corresponding to the second standard view and selecting a middle scan plane in a middle of the range of scan acquisition angles as the additional scan plane 210 having the second standard view. The additional scan plane 210 having the second standard view may be automatically determined 312-316 by the at least one processor 132, 140, 150 by identifying all scan planes having the second standard view and selecting the additional scan plane 210 having the second standard view based at least in part on a closest match to a reference second standard view.

In certain embodiments, the method 300 may comprise automatically adjusting 308, by the at least one processor 132, 140, 150, the scan acquisition angle prior to acquiring the scan plane 210. The automatically adjusting 308 the scan acquisition angle and the acquiring 308 the scan plane 210 is performed iteratively until the scan plane 210 having the first standard view is automatically identified 308 by the at least one processor 132, 140, 150. In an exemplary embodiment, the method 300 may comprise presenting 310, at the display system 134, 200, the scan plane 210 having the first standard view in response to the at least one processor 132, 140 automatically identifying the scan plane 210 as the first standard view.

Various embodiments provide a system 100 for acquiring standard ultrasound scan plane views. The system 100 may comprise an ultrasound probe 104, at least one processor 132, 140, 150, and a display system 134, 200. The ultrasound probe 104 may be positioned at a scan position over a region of interest and may be configured to acquire a scan plane 210 and acquire an additional scan plane 210 at an adjusted scan acquisition angle until a second standard view is determined. The second standard view is different than a first standard view. The at least one processor 132, 140, 150 may be configured to identify the scan plane 210 as the first standard view. The at least one processor 132, 140, 150 may be configured to automatically adjust a scan acquisition angle until the second standard view is determined. Adjusting the scan acquisition angle may comprise at least one of rotating and tilting the scan acquisition angle to provide the adjusted scan acquisition angle. The at least one processor 132, 140, 150 may be configured to automatically determine whether the additional scan plane 100 is the second standard view. The display system 134, 200 may be configured to present the additional scan plane 210 having the second standard view.

In an exemplary embodiment, the system 100 may comprise a user input module 130 and a data storage medium 138. The user input module 130 may be configured to receive instructions. The data storage medium 138 may be configured to store one or both of the scan plane 210 having the first standard view and the additional scan plane 210 having the second standard view. The storage at the data storage medium 138 may be provided automatically, by the at least one processor 132, 140, in response to at least one of the scan plane 210 having the first standard view and the additional scan plane 210 having the second standard view being automatically identified. The storage at the data storage medium 138 may be provided in response to an instruction received via the user input module 130. The storage at the data storage medium 138 may be provided after at least one of the scan plane 210 having the first standard view and the additional scan plane 210 having the second standard view is presented at the display system 134, 200 for a predetermined amount of time. In various embodiments, the at least one processor 132, 140, 150 automatically adjusts the scan acquisition angle and the ultrasound probe 104 acquires the additional scan plane 210 iteratively until the additional scan plane 210 having the second standard view is automatically determined by the at least one processor 132, 140.

In a representative embodiment, the at least one processor 132, 140 may be configured to apply machine learning algorithms to the scan plane 210 to automatically identify the scan plane 210 as the first standard view. The at least one processor 132, 140 may be configured to apply machine learning algorithms to the additional scan plane 210 to automatically determine whether the additional scan plane 210 is the second standard view. In certain embodiments, the at least one processor 132, 140 may automatically determine whether the additional scan plane 210 is the second standard view by selecting a first instance of the additional scan plane 210 having the second standard view. The at least one processor 132, 140 may automatically determine whether the additional scan plane 210 is the second standard view by identifying a range of scan acquisition angles corresponding to the second standard view and selecting a middle scan plane in a middle of the range of scan acquisition angles as the additional scan plane 210 having the second standard view. The at least one processor 132, 140 may automatically determine whether the additional scan plane 210 is the second standard view by identifying all scan planes having the second standard view and selecting the additional scan plane 210 having the second standard view based at least in part on a closest match to a reference second standard view.

In various embodiments, the at least one processor 132, 140, 150 may be configured to automatically adjust the scan acquisition angle prior to acquiring the scan plane 210. The at least one processor 132, 140, 150 may automatically adjust the scan acquisition angle and the ultrasound probe 104 may acquire the scan plane 210 iteratively until the at least one processor 132, 140 automatically identifies the scan plane 210 having the first standard view. In an exemplary embodiment, the display system 134, 200 may be configured to present the scan plane 210 having the first standard view in response to the at least one processor 132, 140 automatically identifying the scan plane 210 as the first standard view.

Certain embodiments provide a non-transitory computer readable medium having stored thereon, a computer program having at least one code section. The at least one code section is executable by a machine for causing the machine to perform steps 300. The steps 300 may comprise acquiring 302 a scan plane 210 from an ultrasound probe 104 positioned at a scan position over a region of interest. The steps 300 may comprise identifying 304, 306 the scan plane 210 as a first standard view. The steps 300 may comprise automatically adjusting 312, 316 a scan acquisition angle until a second standard view is determined 314, 316. Adjusting the scan acquisition angle may comprise at least one of rotating and tilting the scan acquisition angle. The second standard view is different than the first standard view. The steps 300 may comprise acquiring 312, 316 an additional scan plane 210 at the adjusted scan acquisition angle from the ultrasound probe 104 positioned at the scan position until the second standard view is determined 314, 316. The steps 300 may comprise automatically determining 314, 316 whether the additional scan plane 210 is the second standard view. The steps 300 may comprise presenting 318 the additional scan plane 210 having the second standard view at a display system 134, 200.

In an exemplary embodiment, one or both of the scan plane 210 having the first standard view and the additional scan plane 210 having the second standard view is stored 310, 318 at a data storage medium 138. The storage 310, 318 at the data storage medium 138 may occur automatically in response to at least one of the scan plane 210 having the first standard view and the additional scan plane 210 having the second standard view being automatically identified 304-308, 312-316. The storage 310, 318 at the data storage medium 138 may occur in response to an instruction received via a user input module 130. The storage 310, 318 at the data storage medium 138 may occur after at least one of the scan plane 210 having the first standard view and the additional scan plane 210 having the second standard view is presented 310, 318 at the display system 134, 200 for a predetermined amount of time.

In a representative embodiment, the automatically adjusting 312, 316 the scan acquisition angle and the acquiring 312, 316 the additional scan plane 210 is performed iteratively until the additional scan plane 210 having the second standard view is automatically determined 312-316. In certain embodiments, the identifying 304-308 the scan plane 210 as the first standard view may be performed by applying machine learning algorithms to the scan plane 210. The automatically determining 312-316 whether the additional scan plane 210 is the second standard view is performed by applying the machine learning algorithms to the additional scan plane 210.

In various embodiments, the additional scan plane 210 having the second standard view may be automatically determined 312-316 by selecting a first instance of the additional scan plane 210 having the second standard view. The additional scan plane 210 having the second standard view may be automatically determined 312-316 by identifying a range of scan acquisition angles corresponding to the second standard view and selecting a middle scan plane in a middle of the range of scan acquisition angles as the additional scan plane 210 having the second standard view. The additional scan plane 210 having the second standard view may be automatically determined 312-316 by identifying all scan planes having the second standard view and selecting the additional scan plane 210 having the second standard view based at least in part on a closest match to a reference second standard view. In an exemplary embodiment, the steps 300 may comprise automatically adjusting 308 the scan acquisition angle prior to acquiring the scan plane 210. The automatically adjusting 308 the scan acquisition angle and the acquiring 308 the scan plane 210 is performed iteratively until the scan plane 210 having the first standard view is automatically identified 308.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for acquiring standard ultrasound scan plane views.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
    acquiring, by an ultrasound probe positioned at a scan position over a region of interest, a scan plane;
    determining, by the at least one processor, the scan plane is not a first standard view;
    performing, until the first standard view is determined:
        automatically adjusting, by the at least one processor, a scan acquisition angle, wherein adjusting the scan acquisition angle comprises at least one of rotating and tilting the scan acquisition angle by a pre-defined amount, and wherein the pre-defined amount is defined prior to the acquiring the scan plane;
        acquiring, by the ultrasound probe positioned at the scan position, an additional scan plane at the adjusted scan acquisition angle; and
        automatically determining, by the at least one processor, whether the additional scan plane is the first standard view,
        wherein the automatically adjusting the scan acquisition angle and the acquiring the additional scan plane is performed iteratively at the scan position until the additional scan plane having the first standard view is automatically determined by the at least one processor; and
    presenting, at a display system, the additional scan plane having the first standard view.

2. The method of claim 1, wherein the automatically adjusting the scan acquisition angle and the acquiring the additional scan plane is performed automatically after an elapsed time.

3. The method of claim 1, wherein the automatically adjusting the scan acquisition angle and the acquiring the additional scan plane is performed in response to the at least one processor receiving a system assistance instruction.

4. The method of claim 1, wherein the additional scan plane having the first standard view is stored at a data storage medium automatically, by the at least one processor, in response to the additional scan plane having the first standard view a being automatically determined.

5. The method of claim 1, wherein the additional scan plane having the first standard view is stored at a data storage medium in response to an instruction received via a user input module.

6. The method of claim 1, wherein the additional scan plane having the first standard view is stored at a data storage medium after the additional scan plane having the first standard view is presented at the display system for a predetermined amount of time.

7. The method of claim 1, wherein one or both of:
    the determining the scan plane is not the first standard view is performed by the at least one processor applying machine learning algorithms to the scan plane; and
    the automatically determining whether the additional scan plane is the first standard view is performed by the at least one processor applying the machine learning algorithms to the additional scan plane.

8. The method of claim 1, further comprising performing, until a second standard view is determined, wherein the second standard view is different than the first standard view:
    automatically adjusting, by the at least one processor, a second scan acquisition angle, wherein adjusting the second scan acquisition angle comprises at least one of rotating and tilting the second scan acquisition angle by a second pre-defined amount, and wherein the second pre-defined amount is defined prior to the acquiring the scan plane;
    acquiring, by the ultrasound probe positioned at the scan position, a further scan plane at the adjusted second scan acquisition angle; and automatically determining, by the at least one processor, whether the further scan plane is the second standard view,
wherein the automatically adjusting the second scan acquisition angle and the acquiring the further scan plane is performed iteratively at the scan position until the further scan plane having the second standard view is automatically determined by the at least one processor; and
presenting, at the display system, the further scan plane having the second standard view.

9. The method of claim 8, wherein the further scan plane having the second standard view is stored at a data storage medium at least one of:
automatically, by the at least one processor, in response to the further scan plane having the second standard view being automatically determined;
in response to an instruction received via a user input module; or
after the further scan plane having the second standard view is presented at the display system for a predetermined amount of time.

10. The method of claim 8, wherein the automatically determining whether the further scan plane is the second standard view is performed by the at least one processor applying machine learning algorithms to the further scan plane.

11. A system comprising:
an ultrasound probe positioned at a scan position over a region of interest configured to:
acquire a scan plane; and
acquire an additional scan plane at an adjusted scan acquisition angle until a first standard view is determined;
at least one processor configured to:
determine the scan plane is not a first standard view;
automatically adjust a scan acquisition angle until the first standard view is determined, wherein adjusting the scan acquisition angle comprises at least one of rotating and tilting the scan acquisition angle by a pre-defined amount, and wherein the pre-defined amount is defined prior to the acquiring the scan plane; and
automatically determine whether the additional scan plane is the first standard view,
wherein the at least one processor automatically adjusts the scan acquisition angle and the ultrasound probe acquires the additional scan plane iteratively at the scan position until the additional scan plane having the first standard view is automatically determined by the at least one processor; and
a display system configured to present the additional scan plane having the first standard view.

12. The system of claim 11, wherein the at least one processor is configured to automatically adjust the scan acquisition angle and the ultrasound probe is configured to acquire the additional scan plane automatically after an elapsed time.

13. The system of claim 11, wherein the at least one processor is configured to automatically adjust the scan acquisition angle and the ultrasound probe is configured to acquire the additional scan plane in response to the at least one processor receiving a system assistance instruction.

14. The system of claim 11, comprising a data storage medium, wherein the at least one processor automatically stores the additional scan plane having the first standard view at the data storage medium in response to the additional scan plane having the first standard view being automatically determined.

15. The system of claim 11, comprising:
a user input module configured to receive instructions; and
a data storage medium, wherein the at least one processor stores the additional scan plane having the first standard view at the data storage medium in response to an instruction received via the user input module.

16. The system of claim 11, comprising a data storage medium, wherein the at least one processor stores the additional scan plane having the first standard view at the data storage medium after the additional scan plane having the first standard view is presented at the display system for a predetermined amount of time.

17. The system of claim 11, wherein the at least one processor is configured to apply machine learning algorithms to one or both of:
the scan plane to automatically determine the scan plane is not the first standard view; and
the additional scan plane to automatically determine whether the additional scan plane is the first standard view.

18. The system of claim 11, wherein the at least one processor is configured to adjust the scan acquisition angle by rotating the scan acquisition angle.

19. The system of claim 11, wherein the at least one processor is configured to adjust the scan acquisition angle by tilting the scan acquisition angle.

20. The system of claim 11, wherein the at least one processor is configured to adjust the scan acquisition angle by rotating and tilting the scan acquisition angle.

21. A system comprising:
an ultrasound probe positioned at a scan position over a region of interest configured to:
acquire a scan plane;
acquire an additional scan plane at an adjusted scan acquisition angle until a first standard view is determined; and
acquire a further scan plane at an adjusted second scan acquisition angle until a second standard view is determined;
at least one processor configured to:
determine the scan plane is not a first standard view;
automatically adjust a scan acquisition angle until the first standard view is determined, wherein adjusting the scan acquisition angle comprises at least one of rotating and tilting the scan acquisition angle by a pre-defined amount, and wherein the pre-defined amount is defined prior to the acquiring the scan plane;
automatically determine whether the additional scan plane is the first standard view,
wherein the at least one processor automatically adjusts the scan acquisition angle and the ultrasound probe acquires the additional scan plane iteratively at the scan position until the additional scan plane having the first standard view is automatically determined by the at least one processor;
automatically adjust a second scan acquisition angle until the second standard view is determined, wherein adjusting the second scan acquisition angle comprises at least one of rotating and tilting the scan acquisition angle to provide the adjusted second scan acquisition angle by a pre-defined amount, and wherein the pre-defined amount is defined prior to the ultrasound probe acquiring the scan plane; and automatically determine whether the additional scan plane is the second standard view, wherein the at least one processor automatically adjusts the second scan acquisition angle and the ultrasound probe acquires the further scan plane iteratively at the scan position until the further scan plane having the second standard view is automatically determined by the at least one processor; and a display system configured to present the additional scan plane having the first standard view and the further scan plane having the second standard view.

22. The system of claim 21, comprising:

a user input module configured to receive instructions; and a data storage medium configured to store one or both of the additional scan plane having the first standard view and the further scan plane having the second standard view at least one of:

automatically, by the at least one processor, in response to at least one of the additional scan plane having the first standard view and the further scan plane having the second standard view being automatically determined;

in response to an instruction received via the user input module; or after at least one of the additional scan plane having the first standard view and the further scan plane having the second standard view is presented at the display system for a predetermined amount of time.

23. The system of claim 21, wherein the at least one processor is configured to apply machine learning algorithms to:

the scan plane to automatically determine the scan plane is not the first standard view;

the additional scan plane to automatically determine whether the additional scan plane is the first standard view; and/or the further scan plane to automatically determine whether the further scan plane is the second standard view.

* * * * *